United States Patent [19]

Dubeck et al.

[11] 4,062,898
[45] Dec. 13, 1977

[54] CONVERSION OF ACETALS

[75] Inventors: Michael Dubeck, Birmingham; Gordon G. Knapp, Southfield, both of Mich.

[73] Assignee: Ethyl Corporation, Richmond, Va.

[21] Appl. No.: 620,108

[22] Filed: Oct. 6, 1975

[51] Int. Cl.$^2$ ............................................. C07C 29/00
[52] U.S. Cl. ........................ 260/632 B; 260/632 CA
[58] Field of Search ........ 260/632 B, 632 CA, 642 B, 260/450, 449.6

[56] References Cited

U.S. PATENT DOCUMENTS

| | | | |
|---|---|---|---|
| 1,562,480 | 11/1925 | Wietzel et al. | 260/642 B |
| 2,429,878 | 10/1947 | Gresham et al. | 260/449.6 |
| 3,248,432 | 4/1966 | Riley et al. | 260/642 B X |
| 3,285,948 | 11/1966 | Butter | 260/642 B |

FOREIGN PATENT DOCUMENTS 552,803  2/1958  Canada ............................. 260/632 B

*Primary Examiner*—Bernard Helfin
*Attorney, Agent, or Firm*—Donald L. Johnson; Robert A. Linn; Willard G. Montgomery

[57] ABSTRACT

Acetals can be transformed into useful products by reaction with carbon monoxide and hydrogen. For example, methylal can be converted to ethanol and β-methoxyethanol. The reaction can be conducted in the presence of a catalyst system comprising cobalt, iodine and ruthenium.

1 Claim, No Drawings

CONVERSION OF ACETALS

BACKGROUND OF THE INVENTION

Traditionally, ethanol has been made by fermentation processes. Synthetic processes offer promise however, since they utilize less expensive raw materials. It has already been proposed to make ethanol from methanol since the latter substance can be made inexpensively from synthesis gas. U.S. Pat. No. 3,285,948 discusses homologation of methanol.

SUMMARY OF THE INVENTION

A process for the conversion of lower acetals to alcohols which comprises reaction of an acetal with CO and $H_2$. The process can be conducted in the presence of a cobalt catalyst which may also contain iodine and ruthenium components. In a particular embodiment, this invention comprises reaction of methylal

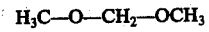

with carbon monoxide and hydrogen in the presence of small but catalytically effective amounts of cobalt iodide and ruthenium chloride, the reaction being conducted at mildly elevated temperature and pressure, whereby ethanol is formed. β-Methoxyethanol can be formed as a co-product.

DESCRIPTION OF PREFERRED EMBODIMENTS

This invention is broadly directed to reaction of CO and $H_2$ with acetals $$R-O-R'-O-R''$$

wherein R, R', and R'' are organic radicals, either alike or different. Preferably, the process entails reaction of lower acetals, since they generally afford yields higher than those obtainable with higher acetals. Thus, a preferred embodiment comprises utilization of acetals which afford acceptable yields of desired products.

The process proceeds well with methylal and the results therewith suggest use of higher substances such as dimethyl acetal, diethyl acetal, and the like. In a preferred embodiment, this invention pertains to reaction of

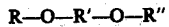

wherein $R_1$, and $R_2$, and the $R_3$ have one or two carbon atoms. Preferably, $R_1$ and $R_3$ are the same, although this is not a critical requirement. When they are the same, higher yields of one or more products are obtainable and the reaction mixtures are not as complex. This minimizes problems associated with fractionation of the reaction mixture into components.

In a particularly preferred embodiment, $R_1$ and $R_3$ are methyl radicals and $R_2$ is methylene or ethylidene. Thus, particularly preferred starting materials are methylal and acetal.

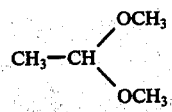

In the process, increase in carbon chain size occurs. This can be illustrated by the formation of ethanol from methylal.

As immediately apparent, a one-carbon fragment yields a product with two carbons. Although not bound by any theory, the increase in carbon chain length can be considered to occur by insertion of a carbonyl group

followed by reduction to a methylene radical.

This increase in carbon chain size can be termed a "homologation."

Generally, this process comprises contacting an acetal, CO, and $H_2$ under reaction conditions. The reaction conditions employed are not critical, and may be varied to accomplish the desired result. They are not truly independent variables, but depend somewhat on the other reaction conditions employed. By way of illustration, a process conducted without a catalyst will generally entail more severe conditions than when a catalyst is employed. Furthermore, the reaction conditions can depend on catalyst strength, reactivity of the reactants, reaction vessel type, and other like conditions.

Thus, in a general aspect, this invention entails reaction conditions selected from the following variables and ranges:
 a. temperature, from about 50° to about 300° C. with from 150° to 250° C being preferred;
 b. pressure, from about 200 to about 10,000 psig, with about 500 to 5,000 psig being preferred;
 c. time, from one-half to eight hours, with from one to four hours being preferred.

As recognized by a skilled practitioner, the above values are not critical and the process of this invention can be conducted under conditions outside the recited ranges.

The pressures given above are for the system as a whole. As apparent, pressure will depend on the combination of pressures of carbon monoxide, hydrogen, and the pressure of reactants, products and any other components at the temperatures employed. Thus, the pressure will depend on the relative amounts of CO and $H_2$.

For the process, these gases may be introduced in equimolar or substantially equimolar amounts as, for example, via use of synthesis gas. The use of equimolar amounts of CO and $H_2$ is not critical and an excess of either gas may be employed. Thus, for example, the $H_2$/CO ratio can be from about 4 : 1 to about 1 : 0.2, with the following being preferred: 2 : 1 to 1 : 0.05. These ratios are not critical and it is possible to operate outside these ranges. For example, if the gases are not introduced at the same rate, as in a staged introduction of one or both gases, the relative amounts can be, at least for a time, outside the ranges given. Thus, it can be said that in a most general aspect, it is generally desirable to introduce enough CO and $H_2$ into the reaction zone to react with the acetal to the extent desired. An excess of CO and or H₂ can be present. For example, an excess of one or the other gas can be used to increase the pressure of the system. With regard to the amount of acetal relative to the amount of CO employed, generally at least two moles of CO per mole of acetal are used. Greater or lesser amounts of either reactant can be utilized, but if an excess of one reactant is desired, usually CO is employed in excess because it is cheaper. Similarly, at least two moles of H₂ is employed per mole of acetal, but greater or lesser amounts can be used. H₂ is cheaper than the acetal and an excess of hydrogen is, therefore, cheaper than an excess of acetal. Consequently, hydrogen excesses, from an economic viewpoint, are more reasonable than an excess of acetal.

The CO and H₂ are employed at the mildly elevated pressures and temperatures discussed above. Generally, these variables have an effect on reaction rate and reaction time, with higher temperatures and pressures generally providing higher reaction rates and shorter times.

Reaction times and rates can be altered by an effective catalyst. Cobalt species are useful catalysts for this invention. The exact cobalt compound employed is not critical so long as it provides the desired effect. Cobalt salts can be used such as the cobalt halides and salts of carboxylic acids, especially the lower acids, e.g., HCOOH, CH₃COOH, CH₃CH₂COOH and the like. Besides the simple salts, complex salts of cobalt can be used. The valence of cobalt is not critical, Co(II) and Co(III) salts are effective.

So are compounds in which Co does not have an electrovalence. Such materials are simple and complex cobalt carbonyls and cobalt carbonyl hydrides.

Although not bound by any theory, it is believed that cobalt carbonyl Co₂(CO)₈ or HCo(CO)₄ are active catalysts in the system, and it is believed that any cobalt species which yield such a molecule under the reaction conditions employed can serve as a catalyst. Thus, the cobalt compounds found useful as catalysts in the oxo reaction are employable in the process of this invention. Likewise, use of

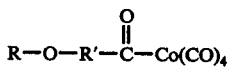

as well as

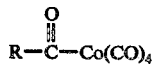

compounds, wherein R and R' are as discussed above and correspond to radicals within the starting acetal are useful in the invention. Cobalt (II) acetate and cobalt (II) iodide are preferred cobalt species for addition to the reaction zone.

Iodine is a preferred component in a catalyst system for this invention; it may be added as a component of the cobalt salt, or as free iodine, or as a component of another salt such as an alkali metal iodide, or by a combination of one or more of these means. A combination of iodine components is preferred, for example, when it is desirable to use iodine promoter in a molar excess of the number of moles of cobalt employed.

In general, the amount of cobalt employed can be from about 0.001 to about 0.5 gram atom of cobalt per each mole of acetal; preferably, about 0.05 to 0.1 gram atom per gram mole of acetal.

The amount of iodine is generally from about 0.02 to about 2 gram atoms of iodine per gram atom of cobalt, preferably about 0.4 to 2.0 gram atoms per gram atom of cobalt.

It is to be understood that the above amounts are not critical and amounts outside these ranges can be used. For example, reaction can occur without cobalt and/or iodine, but better results are obtainable when cobalt is in the reaction system and still better when iodine is used.

The reaction is preferably conducted in the substantial absence of added air and the reaction zone is preferably flushed with CO, H₂, H₂, or two or more of these gases prior to use.

Reaction can be conducted in the presence of substances which do not materially retard the process of cause significant amount of undesirable side reaction to occur. Thus, the process can be conducted in the presence of a hydrocarbon reaction medium such as hexane, heptane, benzene, and the like, or H₂O although preferably the amount of water is below about 20 weight percent of the non-gaseous components present, more preferably, less than 5 weight percent.

The process can be conducted as described above followed by insertion of a hydrogenation catalyst into the reaction zone to complete the reaction. It is unnecessary to conduct the process in this serial fashion and a hydrogenation catalyst such as Ni, Fe, and Ru, can be placed in the reaction system along with the other ingredients. Ruthenium catalysis is preferred and ruthenium metal, ruthenium halide (chloride, bromide, or iodide) are preferred ruthenium species although any active ruthenium-containing species can be used.

When employed, the amount of ruthenium Fe or Ni reduction catalyst is from about 0.0001 to about 0.1 gram atom per each mole of acetal employed; preferably from 0.0005 to 0.05 gram atom.

EXAMPLE I

To the glass liner of a rocking autoclave was added 21.5 g. of methylal. Then, cobalt iodide (1.0 g) and ruthenium chloride (0.1 g) were added. The liner was placed in the autoclave and then pressured with 1500 psi of hydrogen and also 1500 psi of carbon monoxide. The mixture was then heated to 185° and held at that temperature for two hours. After cooling and venting the gases, the dark liquid could be separated by distillation to yield:

| | |
|---|---|
| Water | 13.9 weight per cent |
| Methanol | 16.3 weight per cent |
| Acetaldehyde | 0.2 weight per cent |
| Ethanol | 20.8 weight per cent |
| Methyl acetate | 6.5 weight per cent |
| n-Propanol | 0.6 weight per cent |
| Ethyl acetate | 2.9 weight per cent |
| β-Methoxyethanol + Ethylene glycol | |
| Dimethyl ether | 10.7 weight per cent |
| Ethylene glycol | 0.5 weight per cent |
| Unknown | 0.3 weight per cent |
| Methylal Conversion | 100% |
| Yield Ethanol | 29.5% |

EXAMPLE II

The reaction was repeated as in Example I above except that the reaction time was increased to four hours. During this reaction, when the pressure dropped below 3000 psi, then equal pressures of each hydrogen and carbon monoxide were added to return the pressure to 4000 psi. Separation of the components of the liquid product showed that it had the following composition:

| | |
|---|---|
| Water | 18.9 weight per cent |
| Methanol | 5.9 weight per cent |
| Acetaldehyde | 0.2 weight per cent |
| Ethanol | 24.4 weight per cent |
| Methyl acetate | 7.1 weight per cent |
| n-Propanol | 2.2 weight per cent |
| Ethyl Acetate | 7.8 weight per cent |
| β-Methoxyethanol + Ethylene glycol dimethyl ether | 6.9 weight per cent |
| Ethylene glycol | 0.4 weight per cent |
| Unknown | 1.4 weight per cent |
| Methylal conversion | 100 weight per cent |
| Yield Ethanol | 40.3 % |

In addition there was 11.5 weight percent of non-volatile fraction including 2.6% catalyst.

Similar results are obtained in the processes of the above examples using, one at a time, dimethyl acetal, dimethyl propional, dimethyl butyral, diethyl formal, and dibutyl formal; and reaction temperatures of 150 to 250° C and reaction pressures of 500 to 5000 psig, reaction times of one to four hours, cobalt formate, cobalt carbonyl, cobalt carbonyl hydride, cobalt bromide, and cobalt iodide, one at a time, in a concentration of 0.06 to 0.1 gram atom of cobalt per each gram mole of acetal, NaI, LiI, KI, $I_2$, one at a time, in a concentration of 0.2 to 1.0 gram atom of $I_2$ per gram mole acetal, and Ru, Ru(CO)$_5$, RuCl$_3$, RuI$_2$, one at a time, in a concentration of 0.0005 to 0.05 gram atom Ru per gram mole of acetal.

Also, this invention can be extended to use of substantially the same reaction conditions as discussed above and (a) methyl esters

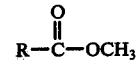

wherein R in the above formula is preferably alkyl, more preferably of 1 to 4 carbon atoms, and b. methyl orthoformate

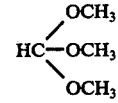

The catalysts can be supported on $Al_2O_3$, $TiO_2$, $SiO_2$, and $Co_2O_3$, or similar supports.

The ethanol produced may be dehydrated to ethylene.

We claim:

1. Process for preparing ethanol, said process comprising reacting methylal with $H_2$ and CO in the presence of a catalyst system comprising cobalt iodide and ruthenium chloride, said process being conducted at a temperature of from about 150° C. to about 250° C. and at a pressure of from about 500 psig to about 5,000 psig, wherein the ratio of $H_2$ to CO is from about 2:1 to about 1:0.05.

* * * * *

UNITED STATES PATENT OFFICE
CERTIFICATE OF CORRECTION

Patent No. 4,062,898     Dated  December 13, 1977

Inventor(s)  Michael Dubeck et al.

It is certified that error appears in the above-identified patent and that said Letters Patent are hereby corrected as shown below:

Column 4, line 14, "$CO, H_2, H_2,$" should read -- $CO, H_2, N_2,$ --.

Signed and Sealed this

Eighth Day of August 1978

[SEAL]

Attest:

RUTH C. MASON
Attesting Officer

DONALD W. BANNER
Commissioner of Patents and Trademarks